United States Patent [19]

Lachnit-Fixson et al.

[11] 4,076,811
[45] Feb. 28, 1978

[54] NOVEL AGENTS AND METHODS FOR TREATMENT OF CLIMACTERIC DISTURBANCES

[75] Inventors: Ursula Lachnit-Fixson; Friedmund Neumann, both of Berlin, Germany

[73] Assignee: Schering Aktiengesellschaft, Berlin and Berkamen, Germany

[21] Appl. No.: 699,192

[22] Filed: Jun. 23, 1976

[30] Foreign Application Priority Data

Jun. 30, 1975  Germany .............................. 2529523

[51] Int. Cl.² ............................................. A61K 31/56
[52] U.S. Cl. ..................................................... 424/239
[58] Field of Search ......................................... 424/239

[56] References Cited

U.S. PATENT DOCUMENTS

| | | | |
|---|---|---|---|
| 3,159,543 | 12/1964 | Ercoli | 424/239 |
| 3,409,721 | 11/1968 | Applezweig | 424/242 |

*Primary Examiner*—Elbert L. Roberts
*Attorney, Agent, or Firm*—Millen & White

[57] ABSTRACT

Reliable relief of physical and psychological menopausal disturbances is achieved by administering a combination of estradiol estrogen or derivatives of estradiol (type 1) and estriol or a derivative of estriol (type 2) in a ratio of approximately 1 : 1 to 1 : 10 for 21 days and thereafter an estrogen of type 2, a placebo or no hormone for 7 days. Administration of the dosage for 28 days permits adaptation to the normal cycle of the female.

5 Claims, No Drawings

NOVEL AGENTS AND METHODS FOR TREATMENT OF CLIMACTERIC DISTURBANCES

BACKGROUND OF THE INVENTION

This invention relates to novel agents and methods for the treatment of physical and psychological climacteric disturbances by estrogen therapy with various natural estrogens.

Climacteric complaints have been treated with a variety of estrogens. Typical cilmacteric or menopausal complaints, such as hot flashes and outbreaks of perspiration, insomnia, cardio-vascular sensations, and sensations of dizziness can be eliminated by daily administration of estradiol valerate for 21 days, followed by a subsequent seven-day hormone-free phase.

Psychic changes, manifesting themselves by emotional imbalance and mood fluctuations, can be eliminated by administration of estradiol valerate. A disadvantage of using estradiol valerate is that the treatment results in extensive proliferations of the endometrium, which leads to undesired uterine bleeding. The strong effect of estradiol valerate on the upper genital tract also limits the use of this substance.

Treatment of climateric disturbances with estriol is conventional. Estriol has a favorable effect on the lower genital tract, i.e., cervix uteri, vagina, and vulva, but has the disadvantage that typical complaints and psychic changes are not satisfactorily ameliorated.

The disadvantages of estradiol valerate and estriol are surprisingly avoided, if selected natural estrogens are administered simultaneously. By a suitable selection of natural estrogens, the effect of the estrogens on the complaints can be increased and the proliferative effect on the uterus can be essentially eliminated. Since considerable synergism in the desired direction is observed simultaneously with an antagonistic effect in the undesired direction, another surprising advantage of selected combinations is that the estrogens can be utilized in a relatively low dosage.

SUMMARY OF THE INVENTION

In a compositional aspect, this invention relates to a composition for the treatment of menopausal disturbances comprising:

a first course of about 21 separate dosage units, adapted for successive daily oral ingestion, consisting essentially of a combination, in admixture with a pharmaceutically acceptable carrier, of an estradiol estrogen and an estriol estrogen, in a ratio of about 1 : 1 to 1 : 10 wherein the estradiol estrogen in each separate dosage unit corresponds in activity to 0.5 – 2 mg. of estradiol valerate;

and, optionally, followed by a second course of about 7 separate dosage units, adapted for successive daily oral ingestion, of the same or different estriol estrogen, corresponding in activity to 1 – 8 mg. of estriol, or a placebo, in admixture with a pharmaceutically acceptable carrier.

In a method-of-use aspect, this invention relates to a method of alleviating the physiological and psychological distrubances of menopause comprising administering for about 21 successive days to a female afflicted therewith a first course of dosage units, in admixture with a pharmaceutically acceptable carrier, of an estradiol estrogen and an estriol estrogen in a ration of about 1 : 1 to about 1 : 10, wherein the estradiol estrogen in each daily dosage unit corresponds in activity to 0.5 – 2 mg. of estradiol valerate, followed by about 7 days without hormone administration, with administration of a placebo, or with successive daily administration of the same or different estriol estrogen, in admixture with a pharmaceutically acceptable carrier, corresponding in activity to 1 – 8 mg. of estriol.

DETAILED DESCRIPTION

Natural estrogens with a strong effect on menopausal disturbances and on the upper genital tract are estradiol and derivatives thereof (type 1 ). Derivatives mean compounds produced by esterification or etherification of estradiol. Esters are derived from estradiol and an organic acid, e.g., a carboxylic acid containing up to 15 carbon atoms, especially an aliphatic carboxylic acid, e.g., an alkanoic acid of 2 – 12 carbon atoms, which can be unsaturated, branched, polybasic, or substituted in the usual manner, for example, by hydroxy or halogen; a cycloaliphatic, aromatic and mixed aromatic-aliphatic (alkaryl and aralkyl) acid, which can likewise by substituted in the usual manner. Examples of equivalent acids are caproic acid, enanthic acid, undecyclic acid, oleic acid, dichloroacetic acid, cyclopentylpropionic acid, phenylpropionic acid, phenylacetic acid, phenoxyacetic acid, succinic acid, benzoic acid; others being acids containing 1 – 18, preferably 2 – 12 carbon atoms, including aliphatic acids containing 1 – 18, preferably 1 – 6 carbon atoms, e.g., valeric, α-ethylvaleric, isovaleric, 2-ethylbutyric, butyric, 3-ethylbutyric, hexanoic, diethylacetic, triethylacetic, octanoic, undecyclic and palmitic acids; a cyclic acid, preferably a cycloaliphatic acid, containing, e.g., 5 – 18 carbon atoms, e.g., cyclopropylideneacetic, cyclobutylcarboxylic, cyclopentylcarboxylic, cyclopentylacetic, cyclohexylacetic, and β-cyclohexylpropionic acids; a carbocyclic aryl or alkaryl acid, e.g., containing 6 – 18 carbon atoms, and 1 to 5, preferably 1 or 2 rings, e.g., benzoic, 2-, 3-, or 4-methylbenzoic, 2,3-, 2,4-, 2,5-, 2,6-, 3,4- and 3,5-dimethylbenzoic, ethylbenzoic, 2,3,6-trimethylbenzoic and 3-methyl- α-naphthoic acids; an aralkyl acid, e.g., containing 7 to 18 carbon atoms, e.g., β- phenylpropionic, a polybasic acid, e.g., containing 2 – 18 carbon atoms and, optionally, 1 to 5 hydroxy groups, e.g., glycolic, lactic, citric, succinic, tartaric, d-maleic, d-gylceric, glutaric and salicyclic acids; and the corresponding acids containing one, two or more of simple substituents, e.g., halo, alkoxy, acyloxy, etc., in the molecule, e.g., chloroacetic, fluoroacetic, trichloroacetic, trifluoroacetic, 2,3,4-trimethoxybenzoic, phenoxyacetic, α- naphthoxyacetic acids.

Esters of estradiol considered equivalent to estradiol are derived from alkanols corresponding to the organic acids above.

Esters of estradiol, such as estradiol valerate are preferred.

Natural estrogens having a lesser effect on the disturbances and a strong effect on the lower genital tract are estriol and derivatives thereof (type 2). Derivatives mean ethers and esters of estriol. Ethers and esters considered equivalent to estriol include those considered as equivalent to estradiol, above. Estriol and estriol succinate are preferred.

The invention accordingly relates to novel agents for the treatment of climacteric disturbances, consisting of two phases, wherein agents used in the first phase are administered in daily dosage units, including carriers, flavor-ameliorating agents and/or fillers customary in galenic pharmacy, of a combination of an estrogen of type 1 and an estrogen of type 2 in a ratio of approximately 1 : 1 to 1 : 10 (ratio by weight) and agents used in the second phase are given in 7 daily dosage units including carriers, flavor-ameliorating agents and/or fillers customary in galenic pharmacy, of an estrogen of type 2.

This invention also relates to compositions for treatment of climacteric disturbances consisting of 21 daily dosage units, including the carriers, flavor-ameliorating agents and/or fillers customary in galenic pharmacy, of an estrogen of type 1 and an estrogen of type 2 in a ratio of approximately 1 : 1 to 1 : 10 (ratio by weight).

It will be understood that the first phase can vary from 19 to 23 days and the second phase from 5 to 9 days, so that a cycle of the first and second phases will be about 28 days.

This invention concerns a novel method for the treatment of climacteric disturbances, wherein a combination of an estrogen of type 1 and an estrogen of type 2 is administered in a ratio of approximately 1 : 1 to 1 : 10 daily for 21 days and subsequently an estrogen of type 2 and no hormone at all is administered daily for 7 days.

Especially suitable as estrogens of type 1 are estradiol and esters of estradiol. The type 1 estrogen utilized is preferably administered in such quantities that the amount administered according to the invention during the first 21 days corresponds in activity to daily administration of 0.5 – 2 mg. of estradiol valerate.

Suitable estrogens of type 2 are estriol and esters of estriol. The estrogen of type 2 utilized is administered in such quantities that the amount administered during the first 21 days corresponds in activity to daily administration of 1 – 8 mg. of estriol. The amount of natural estrogen optionally utilized in the 7 days of the second phase is equal to that corresponding to daily administration of 1 – 8 mg. of estriol.

Estrogens of type 2 used according to this invention in the first and second phases can be identical or different.

The estrogenic components are preferably given together orally, but they can be administered separately or parenterally. The active agents are processed together with additives, carriers and/or flavor-ameliorating agents conventional in galenic pharmacy into the customary forms of application by known methods. For oral dosages, tablets, dragees, capsules, pills, suspensions, or solutions are especially suitable. For parenteral application oily solutions, e.g., sesame oil or caster oil solutions, which can also contain a diluent, for example, benzyl benzoate or benzyl alcohol, are used.

The menopausal composition adapted for oral ingestion can be provided as a packaged sequence of unit dosage forms adapted for oral ingestion of one unit dosage form of estradiol estrogen and estriol estrogen daily in sequence for 19-23 days, preferably 21 days, preferably followed in sequence by about 5-9 placebos or unit dosage forms of estriol estrogen to provide a total of 28 unit dosages per package. The unit dosages are preferably packaged in the conventional bubble plastic package having 28 bubbles in a sheet of flexible plastic arranged in an oval or circle, each containing a unit dosage with the placebos or estriol dosages being positioned so as to be ingested last. The bubbles are sealed by a frangible sheet which is adapted to break and release the unit dosage when the bubble is pressed.

Without further elaboration, it is believed that one skilled in the art can, using the preceding description, utilize the present invention to its fullest extent. The following preferred specific embodiments are, therefore, to be construed as merely illustrative, and not limitative, of the remainder of the disclosure in any way whatsoever.

EXAMPLE 1

| (Composition of a Dragee for each Phase) | | |
|---|---|---|
| 1st Phase: | 1.000 mg. | Estradiol valerate |
| | 2.000 mg. | Estriol |
| | 43.500 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, which is supplemented with customary sugar mixture to about 140 mg. |
| 2nd Phase: | 1.000 mg. | Estriol |
| | 45.500 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, which is supplemented with customary sugar mixture to about 140 mg. |

EXAMPLE 2

| (Composition of a Dragee for each Phase) | | |
|---|---|---|
| 1st Phase: | 0.500 mg. | Estradiol valerate |
| | 4.000 mg. | Estriol |
| | 42.000 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, which is supplemented with customary sugar mixture to about 140 mg. |
| 2nd Phase: | 2.000 mg. | Estriol |
| | 44.500 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, which is supplemented with customary sugar mixture to about 140 mg. |

EXAMPLE 3

| (Composition of a Dragee for each Phase) | | |
|---|---|---|
| 1st Phase: | 1.000 mg. | Estradiol valerate |
| | 4.000 mg. | Estriol |
| | 41.332 mg. | Lactose |
| | 26.800 mg. | Corn starch |
| | 3.000 mg. | Polyvinylpyrrolidone 25 |
| | 0.160 mg. | Methylparaben |
| | 0.008 mg. | Propylparaben |
| | 3.700 mg. | Talc |
| | 80.000 mg. | Total weight, which is supplemented with customary sugar mixture to 140 mg. |
| 2nd Phase: | 2.000 mg. | Estriol |
| | 44.332 mg. | Lactose |
| | 26.800 mg. | Corn starch |
| | 3.000 mg. | Polyvinylpyrrolidone 25 |
| | 0.160 mg. | Methylparaben |
| | 0.008 mg. | Propylparaben |
| | 3.700 mg. | Talc |
| | 80.000 mg. | Total weight, which is supplemented with customary sugar mixture to 140 mg. |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of alleviating the physiological and psychological disturbances of menopause comprising administering for about 21 successive days to a female afflicted therewith a first course of dosage units, in admixture with a pharmaceutically acceptable carrier, of an estradiol estrogen and an estriol estrogen in a ratio of about 1 : 1 to about 1 : 10, wherein the estradiol estrogen in each daily dosage unit corresponds in activity to 0.5 –2 mg. of estradiol valerate, followed by about 7 days without hormone administration, with administration of a placebo, or with successive daily administration of the same or different estratriol estrogen, in admixture with a pharmaceutically acceptable carrier, corresponding in activity to 1 –8 mg. of estriol.

2. The method of claim 1, wherein said estradiol estrogen and the estriol estrogen are administered orally.

3. The method of claim 1, wherein said estradiol estrogen and the estriol estrogen are administered in admixture.

4. The method of claim 1, wherein said estradiol estrogen is estradiol valerate and the estriol estrogen is estriol.

5. The method of claim 1, wherein 0.5 – 2 mg. of estradiol valerate and 1 –8 mg. of estriol are administered daily for 21 days, followed by 1 – 8 mg. of estriol administered daily for 7 days.

* * * * *